United States Patent [19]

Kiri et al.

[11] Patent Number: 4,868,393
[45] Date of Patent: Sep. 19, 1989

[54] RADIATION IMAGE DETECTING APPARATUS

[75] Inventors: Motosada Kiri; Takeshi Matsuoka, both of Koyoto, Japan

[73] Assignee: Shimadzu Corporation, Kyoto, Japan

[21] Appl. No.: 33,030

[22] Filed: Mar. 31, 1987

[30] Foreign Application Priority Data

Aug. 19, 1986 [JP] Japan .................... 61-193052

[51] Int. Cl.$^4$ .............................................. G01T 1/24
[52] U.S. Cl. ................... 250/370.15; 378/146; 378/62
[58] Field of Search ............... 378/99, 146, 199, 200, 378/141, 142; 250/352, 370 L, 370 GX, 214 C, 214 DC, 336.1, 369, 238; 307/491, 310

[56] References Cited

U.S. PATENT DOCUMENTS

| | | | |
|---|---|---|---|
| 3,720,835 | 3/1973 | Pruett | 250/370 L |
| 3,743,835 | 7/1973 | Koncen | 250/370 L |
| 3,746,873 | 7/1973 | Williams | 250/352 |
| 3,780,291 | 12/1973 | Steinet et al. | 378/146 |
| 3,858,056 | 12/1974 | Melamed et al. | 250/214 DC |
| 3,963,926 | 6/1976 | Borrello | 250/370 L |
| 4,421,985 | 12/1983 | Billingsley et al. | 250/352 |
| 4,456,826 | 6/1984 | Forster | 250/370 L |
| 4,472,822 | 9/1984 | Swift | 378/146 |

FOREIGN PATENT DOCUMENTS

1951692 4/1971 Fed. Rep. of Germany ... 250/370 L

OTHER PUBLICATIONS

Derenzo, Stephen E., *Gamma-Ray Spectioscopy Using Small, Cooled Bismuth Germinate Scintillators and Silicon Photodiodes*, Nuclear Instruments and Methods in Physics Research 219 (1984) 117-122.

*Primary Examiner*—Carolyn E. Fields
*Assistant Examiner*—Joseph A. Hynds
*Attorney, Agent, or Firm*—Koda and Androlia

[57] ABSTRACT

In a radiation detecting apparatus having its radiation receiving section composed of two-dimensional or one-dimentional array of radiation sensors, the whole electronic circuit is classified into a temperature-sensitive circuit portion and a temperature-insensitive circuit portion for keeping at least the temperature-sensitive circuit portion at a substantially constant temperature also during the period in which the apparatus is kept standing for detecting a radiation image. For the purpose, at least the above temperature-sensitive circuit portion is kept energized even when a radiation image is not detected; kept warmed by a heating element energized only when a radiation image is not detected, made to get in touch with a heat sink intermittently; or blown at least intermittently by a blower or blowers.

9 Claims, 2 Drawing Sheets

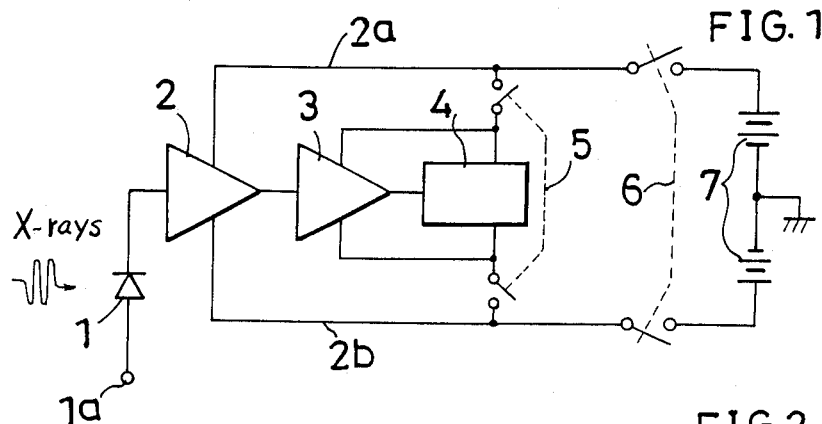
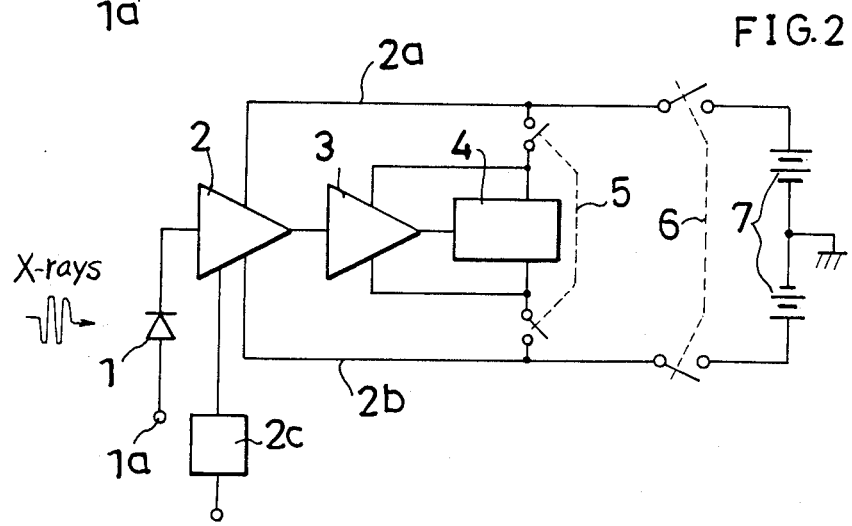
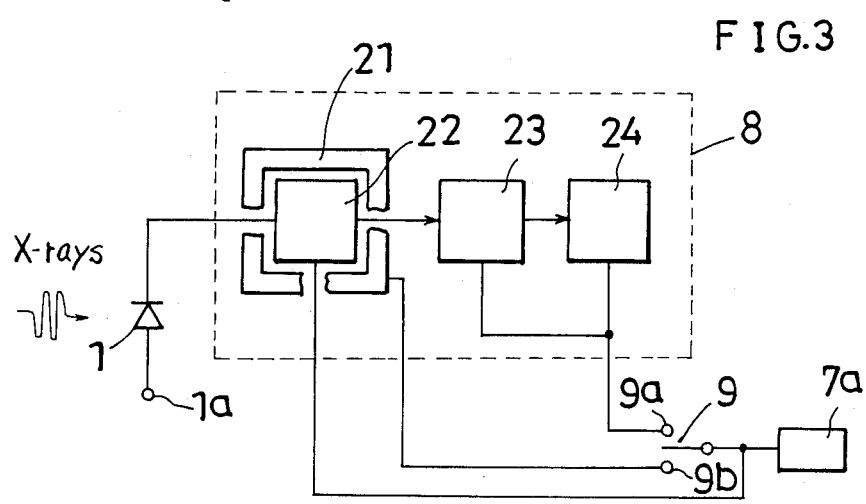

RADIATION IMAGE DETECTING APPARATUS

BACKGROUND OF THE INVENTION

The present invention relates to a radiation image detecting apparatus having its radiation receiving section made up of arrayed radiation sensors.

In a method of electronically detecting a radiation image, the radiation receiving portion consists either of a one-dimensionally arrayed radiation sensors devised so as to scan an image plane or of a two-dimensionally arrayed sensors fixed at an image plane. Each of the radiation sensors is either a single semiconductor sensor or a radiation scintillator combined with a photosensor. In any case each sensor, which converts the radiations incident thereon to electric pulse signals, is followed by an amplifier, a signal discriminator and a counter. The counter counts the number of the pulse signals (pulses) outputted from the counter in the form of a digital signal. Similar radiation intensity signals from all of the counters belonging the arrayed radiation sensors are purposefully treated by a common picture-signal forming circuit, which provides a picture signal to a CRT to make it display a radiation image. Radiation image detecting apparatus based on such a method as mentioned above are disclosed, for example, in the Japanese Laid-open Patent Application No. 59-94046 and European Patent Publication EP-O-137-487-A2.

The apparatus so devised as mentioned above have an important problem to be solved in regard of protecting the constituent circuits from being unfavorably affected by the heat dissipated by the circuits themselves. Suppose that the power consumption per sensor consists of 140 mW at the amplifier, 100 mW at the signal discriminator and 10 mW at the counter, making a total of 250 mW. A one-dimensional array of 1000 sensors, for example, causes an overall heat dissipation of 250 W. This value estimated with 1000 sensors supposed may further increase by several times to some hundred times or more, if the sensors are increased in number for making the image resolving power higher or for constituting the arrayed sensors in two-dimension. In case the radiation image to be detected is, for instance, an X-ray image for diagnosis, one shot of the detection takes only one second or less, and therefore, if a very small number of images are enough for the diagnosis, there is no problem in substance. It is, however, not rare that several tens of images are needed for the diagnosis of one desease. In such a case, if competent measures are not provided to protect the circuits from the heat effect, a series of the X-ray image detection work must be interrupted frequently for cooling the circuits. This not only lowers the efficiency of the image detection work but also keeps the patient under an unpleasant condition for a long time.

OBJECTS AND SUMMARY OF THE INVENTION

The present invention aims at solving such a disadvantageous problem as mentioned above with respect to the known radiation image detecting apparatus having its radiation receiving section made up of arrayed radiation sensors, and makes it an object to provide such an apparatus improved in protecting the constituent circuit from the unfavorable heat effect.

Another object of the present invention is to constitute such an improved apparatus so that the same may be operated continually for a long time.

A further object of the present invention is to make it possible to apply the merits of the invention both to the apparatus in which said arrayed radiation sensors form a two-dimensional matrix-shaped radiation receiving plane and to the apparatus in which said arrayed radiation sensors form a one-dimensional (linear) radiation receiving element made to sweep an image plane on which a radiation image to be detected is formed.

To achieve the above objects, in case the arrayed radiation sensors constituting the radiation receiving section of the apparatus are in the form of a matrix fixed in a plane on which a radiation image is formed, a whole circuit accompanying the radiation sensors for the purpose of deriving an image signal from the signals outputted from the sensors is divided into a temperature-sensitive and a temperature-insensitive circuit portions either to make them capable of being separately energized through their respective power switches operable independently of each other, or to make only the temperature-sensitive circuit portion surrounded with a heat generating element. In such constitution of the whole circuit, only the temperature-sensitive circuit portion is always kept warmed either with the same kept energized or with a current supplied to the heat generating element.

In case the arrayed radiation sensors constituting the radiation receiving section of the apparatus are constituted in the form of a one-dimensional array made movable within a predetermined stroke of movement for sweeping a plane on which a radiation image is formed, a cooling means is provided at least at one end of the stroke of movement in order to cool the circuit (especially its temperature-sensitive portion) accompanying the radiation sensors. The cooling means is a wind fan, a heat sink or the like.

BRIEF EXPLANATION OF THE DRAWINGS

The present invention is further desscribed in detail in the following on reference to the accompanying drawings, in which:

FIG. 1 shows a blockdiagrammatic constitution of the unit circuit per sensor used in an embodiment of the present invention;

FIG. 2 shows a blockdiagrammatic constitution of the unit circuit per sensor used in another embodiment of the present invention;

FIG. 3 shows a blockdiagrammatic constitution of the unit circuit used in a further embodiment of the present invention;

DETAILED DESCRIPTION OF THE INVENTION

Figure 4:
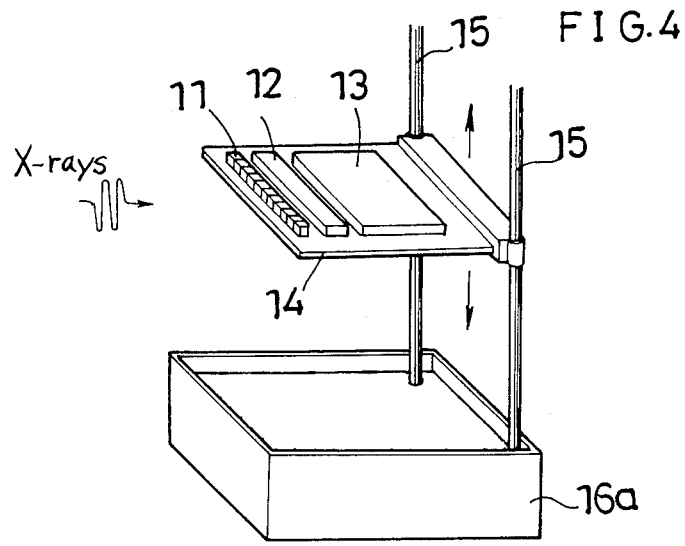
FIG. 4 shows a perspective view of an embodiment of another mode of the present invention.

Referring to FIG. 1, which shows one X-ray detecting unit, an X-ray sensor 1 (corresponding to one picture element: a pixel) composed of a single X-ray sensing device is accompanied by an analog amplifier 2, a pulse discriminator 3 (analog circuit) and a picture (element) signal forming circuit 4, which is a digital circuit wih a counter included therein. Many such X-ray detecting units as shown in FIG. 1 are assembled with the X-ray sensors 1 arranged in the form of a matrix, on which an X-ray image to be detected is projected.

In the above constitution of the X-ray detecting unit (FIG. 1) the X-ray sensor 1, biased with minus several tens to hundreds of volts through a bias terminal 1a, outputs an electric pulse signal consisting of pulses whose number is equal or proportional to the X-ray photons incident on the sensor 1. The pulse signal outputted from the X-ray sensor 1 is amplified by the amplifier 2 and then inputted to the pulse discriminator 3, which trims the height and ground level of the pulses and then outputs them toward the picture element signal forming circuit 4. This circuit 4 makes a picture element signal in the form of a digital signal form the pulse signal originally outputted from the X-ray sensor 1. Such picture element signals from all of the X-ray detecting units assembled with their X-ray sensors constituting the X-ray image receiving plane are used to display a detected X-ray image on a CRT (not shown). The circuit leading the picture element signals to the CRT from the picture element signal forming circuit 4 is not shown in FIG. 1, because it has no relation to the description of the features of the present invention.

In the above-described process of signal treatment, the performance of the analog amplifier 2 is expected to be very stable because, for instance, a small zero-level drift due to temperature variations may cause the amplifier 1 to misdetect the pulse signal from the X-ray sensor 1. On the other hand, the pulse discriminator 3 and the picture element signal forming circuit 4 are not so sensitive to temperature. Therefore, it is very important for a reliable operation of the apparatus to keep the amplifier 1 as free as possible from temperature variations. Since such temperature variations are caused mainly by intermittently switching the power to the circuit, namely, to the amplifier 2 in the present case, the embodiment shown in FIG. 1 is devised so that the amplifier 2 and the group of other circuits 3 and 4 may be separately supplied with power. For the purpose, power supply lines 2a and 2b to the amplifier 2 are connected to a power source 7 only through a main switch 6, whereas the pulse level limitter 3 and picture element signal forming circuit 4 are power-supplied through both the main switch 6 and another switch 5 located inside the main switch 6. In such a wiring constitution of the power supply, it is possible to keep only the amplifier 2 always at a substantially constant temperature, though higher than an ambient temperature, by keeping the switch 6 turned on even while the apparatus is standing for detecting one image in a series of many X-ray images to be detected. On the other hand, the pulse discriminator 3 and the picture element signal forming circuit 4 are power-supplied through the switch 5 only when an X-ray image is practically detected. The amplifier 2 is thus protected from the adverse effect of temperature variations, assuring the apparatus to function properly and reliably.

FIG. 2 shows a modification of the embodiment shown in FIG. 1 In this modified embodiment, the amplifier 2 has its bias controlled by a bias control circuit 2c, which, devised to operate synchronously with the operation of the switch 5, lowers the bias current of the amplifier 2 while the apparatus is standing for image detection. The lowering of the bias current saves energy consumption and decreases the temperature rise in average. A reference sign 2d represents a terminal for receiving a bias control instruction signal.

Another embodiment, which is suitable for constituting the electronic circuit portion of the X-ray detecting unit in the form of a monolithic integrated circuit, is described in the following on reference to FIG. 3. Blocks 22, 23 and 24 represent integrated circuits corresponding respectively to the amplifier 2, pulse discriminator 3 and picture element signal forming circuit 4 of FIG. 1, and constitute the electronic circuit portion 8 of an X-ray detecting unit. An enclosure-shaped element 21 is a heating element characteristic of this embodiment. The heating element 21 is made of a resistive or semiconductive material deposited around the amplifier portion 22 so as to enclose the same. In such constitution of the whole circuit, the amplifier 22 is kept always power-supplied directly from a power source 7a, while the other circuit portions 23 and 24 are energized with a switch 9 turned to a contact 9a only when an X-ray image is detected. The heating element 21 is kept switched off during the detection of an X-ray image. On the other hand, while the aparatus is standing for the next detection of X-ray images, the switch 9 is turned to a contact 9b to supply power to the heating element 21, making the same generate a heat necessary to keep the amplifier 22 at a constant temperature substantially equal to the temperature when the amplifier 22 was warmed also by the heat dissipation from the circuit portions 23 and 24. In the present embodiment, the heating element 21 can be constituted in the form of a power transistor.

In the descriptions regarding to the above embodiments, the temperature-sensitive circuit portion which is to be kept at a constant temperature has been restricted to an amplifier. It goes without saying, however, that the above-described measures for keeping a circuit at a constant temperature may be applied to any other circuits.

In the following, another mode of the present invention is described on reference to FIGS. 4 and 5.

Referring to FIG. 4, a one-dimensional array of X-ray sensors 11 is mounted of a common base plate 14 together with electronic circuit portions 12 and 13, the former containing trains of analog amplifiers and pulse level limitters, and the latter containing picture signal forming digital circuits including pulse counters. The base plate 14 is devised so as to be moved vertically in a predetermined region by a known suitable driving mechanism (not shown), so that the one-dimensional array of X-ray sensors 11 may sweep an image plane on which an X-ray image is projected. At the lowest position of the base plate movement, there is provided a heat sink 16a so as to get in touch with the base plate 14 when it reaches the lower end of the movement. The heat sink 16a is constituted with a liquid coolant reservoir containing such a non-volatile and electrically insulating liquid as silicon oil. The base plate 14 is made preferably to have a large heat capacity. In this embodiment, while the apparatus is kept standing for the detection of an X-ray image, the whole electronic circuit portions 12 and 13 are cooled down enough to be protected from being heated up to an unfavorable value of temperature while the base plate 14 is apart from the heat sink 16a in the course of making the X-ray sensors 11 scan the X-ray image plane.

Figure 5:
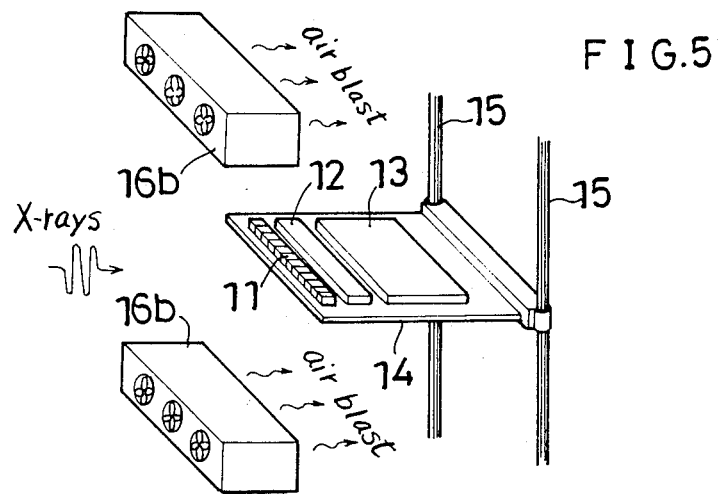
FIG. 5 shows a perspective view of another embodiment of said another mode of the present invention.

FIG. 5 shows another embodiment based on the similar principle on which the above embodiment shown in FIG. 4 is based. in FIG. 5 all the constituents corresponding to those shown in FIG. 4 are indicated with the same reference numbers as those used in FIG. 4. A sole difference of this embodiment from that shown in FIG. 4 is that the heat sink 16a of FIG. 4 is replaced with two air blowers 16b which are furnished at the upper and the lower ends of the base plate movement. In FIGS. 4 and 5, a reference number 15 indicates guide means for guiding the movement of the base plate 14.

As is easily understood from the above descriptions, the present invention improves the X-ray image detecting apparatus with arrayed X-ray sensors so as to function stably without intermission during a substantially continuous operation for detecting a series of many X-ray images.

We claim:

1. A radiation image detecting apparatus having its radiation receiving section comprising an array of radiation sensors, whose output signals are converted to an image signal by an accompanying signal-treating circuit, which comprises a temperature-sensitive circuit portion and a temperature-insensitive circuit portion, said apparatus comprising:
   a first switching means for supplying circuit heating electric power to said temperature-sensitive circuit portion to keep said temperature sensitive circuit portion always warmed while a radiation image detection is not being carried out; and
   a second switching means for supplying an electric power to energize at least said temperature-insensitive circuit portion only while a radiation image detection is being carried out.

2. An apparatus as defined in claim 1, wherein said heating electric power is the electric power to energize said temperature-sensitive circuit portion itself.

3. An apparatus as defined in claim 2, wherein said heating electric power is supplied also to a heat generating element additionally provided surrounding said temperature-sensitive circuit portion 4. An apparatus as defined in claim 3, wherein said heat generating element is made of a resistive material.

5. An apparatus as defined in claim 3, wherein said heat generating element is made of a semiconductive material.

6. A radiation image detecting apparatus having its radiation receiving section comprising a one dimensional array of radiation sensors, whose output signals are converted to an image signal by an accompanying signal-treating circuit, which is, together with said one-dimensional array of radiation sensors, mounted on a common supporting means said apparatus including means for moving said common supporting means within a predetermined stroke of movement so that said one-dimensional array of radiation sensors may scan a plane on which a radiation image is formed, said apparatus comprising:
   a cooling means for cooling said signal treating circuit, said cooling means provided at least at one end of said predetermined stroke of movement.

7. An apparatus as defined in claim 6, wherein said cooling means is an air blower.

8. An apparatus as defined in claim 6, wherein said cooling means is a heat sink made capable of having a thermal contact with said common supporting means when the common supporting means reaches an end of said predetermined stroke of movement.

9. An apparatus as defined in claim 8, wherein said heat sink is made of a liquid coolant reservoir.

* * * * *

UNITED STATES PATENT AND TRADEMARK OFFICE
CERTIFICATE OF CORRECTION

PATENT NO. : 4,868,393

DATED : September 19, 1989

INVENTOR(S) : Motosada Kiri, et al.

It is certified that error appears in the above-identified patent and that said Letters Patent is hereby corrected as shown below:

On the title page,
   Item [75] Inventors: Change "Motosada Kiri; Takeshi Matsuoka, both of Koyoto, Japan" to --Motosada Kiri; Takeshi Matsuoka, both of Kyoto, Japan--

Signed and Sealed this

Eighth Day of January, 1991

Attest:

HARRY F. MANBECK, JR.

*Attesting Officer*     *Commissioner of Patents and Trademarks*